US009283171B2

(12) United States Patent
Florence et al.

(10) Patent No.: US 9,283,171 B2
(45) Date of Patent: *Mar. 15, 2016

(54) COSMETIC FORMULATION

(71) Applicant: MARY KAY INC., Dallas, TX (US)

(72) Inventors: Tiffany Florence, Dallas, TX (US); Michelle Hines, Hickory Creek, TX (US); David Gan, Southlake, TX (US); Barbara Durkee, Carrollton, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/491,624

(22) Filed: Sep. 19, 2014

(65) Prior Publication Data

US 2015/0099018 A1  Apr. 9, 2015

Related U.S. Application Data

(63) Continuation of application No. 13/762,929, filed on Feb. 8, 2013, now Pat. No. 8,877,259.

(60) Provisional application No. 61/596,990, filed on Feb. 9, 2012, provisional application No. 61/597,011, filed on Feb. 9, 2012.

(51) Int. Cl.

| *A61K 36/00* | (2006.01) |
| *A61K 8/97*  | (2006.01) |
| *A61Q 19/00* | (2006.01) |
| *A61Q 1/14*  | (2006.01) |
| *A61Q 19/10* | (2006.01) |

(52) U.S. Cl.
CPC . *A61K 8/97* (2013.01); *A61K 8/975* (2013.01); *A61Q 1/14* (2013.01); *A61Q 19/00* (2013.01); *A61Q 19/10* (2013.01); *A61K 2800/5922* (2013.01)

(58) Field of Classification Search
CPC .. A61K 8/97; A61K 2800/5922; A61K 8/975
See application file for complete search history.

(56) References Cited

U.S. PATENT DOCUMENTS

| 4,211,577 A | 7/1980 | Wallin | 8/646 |
| 4,302,200 A | 11/1981 | Yokoyama et al. | 8/438 |
| 4,409,254 A | 10/1983 | Garin et al. | 426/540 |
| 4,749,573 A | 6/1988 | Bonne et al. | 424/401 |
| 4,996,196 A | 2/1991 | Mitsuhashi et al. | 514/53 |
| 5,089,410 A | 2/1992 | Murata et al. | 435/41 |
| 5,147,861 A | 9/1992 | Della Valle | 514/54 |
| 5,431,911 A * | 7/1995 | Reynolds | 424/401 |
| 5,560,916 A | 10/1996 | Koulbanis et al. | 424/401 |
| 5,595,756 A | 1/1997 | Bally et al. | 424/450 |
| 5,804,168 A | 9/1998 | Murad | 424/59 |
| 5,942,231 A | 8/1999 | Hamada et al. | 424/774 |
| 5,972,993 A | 10/1999 | Ptchelintsev | 514/449 |
| 6,103,240 A | 8/2000 | Zhou | 424/757 |
| 6,124,442 A | 9/2000 | Zhou et al. | 536/4.1 |
| 6,147,054 A | 11/2000 | Ambrosi | 514/23 |
| 6,159,484 A | 12/2000 | Kilian et al. | 424/401 |
| 6,210,692 B1 | 4/2001 | Lorant | 424/401 |
| 6,217,913 B1 | 4/2001 | Mohammadi | 424/520 |
| 6,296,859 B1 | 10/2001 | Stoltz | 424/401 |
| 6,319,523 B1 | 11/2001 | Zhou | 424/725 |
| 6,416,806 B1 | 7/2002 | Zhou | 426/590 |
| 6,468,564 B1 | 10/2002 | Riley et al. | 424/776 |
| 6,524,599 B2 | 2/2003 | Pinnell | 424/401 |
| 6,589,514 B2 | 7/2003 | Jensen | 424/401 |
| 6,623,745 B2 | 9/2003 | Borgnine | 424/401 |
| 6,649,178 B2 | 11/2003 | Mohammadi et al. | 424/401 |
| 6,664,225 B2 | 12/2003 | Mumoli | 510/446 |
| 6,680,062 B2 | 1/2004 | Muizzuddin et al. | 424/401 |
| 6,699,900 B2 | 3/2004 | Zielinski | 514/452 |
| 6,773,743 B1 | 8/2004 | Singer | 426/658 |
| 6,783,754 B2 | 8/2004 | Mankovitz | 424/59 |
| 6,905,696 B2 | 6/2005 | Marotta et al. | 424/401 |
| 6,913,769 B2 | 7/2005 | Oslick et al. | 424/725 |
| 7,048,960 B2 | 5/2006 | Pizzey | 426/629 |
| 7,151,079 B2 | 12/2006 | Fack | 510/121 |
| 7,172,774 B2 | 2/2007 | Leko | 424/764 |
| 7,205,010 B2 | 4/2007 | Sha | 424/756 |
| 7,374,748 B2 | 5/2008 | Di Pierro | 424/59 |
| 7,384,919 B2 | 6/2008 | Benesova et al. | 514/22 |
| 7,399,783 B2 | 7/2008 | Rosenbloom | 514/457 |
| 7,439,269 B2 | 10/2008 | Clarot | 514/738 |

(Continued)

FOREIGN PATENT DOCUMENTS

| CN | 101129311 | 2/2008 |
| JP | 2243613 | 9/1990 |

(Continued)

OTHER PUBLICATIONS

The International Dermal Institute (IDI), Glossary, 'Hydrolyzed Algin', Online, URL< https://web.archive.org/web/20110114030754/http://dermalinstitute.com/us/library/glossary.html?I=H>, Jan. 14, 2011, 2 pages.*
Wikipedia: Guava; Online, URL< http://en.wikipedia.org/wiki/Guava> 8 pages, accessed Feb. 23, 2015.*
Wyatt et al. Phytochemical Analysis and Biological Screening of Leaf and Twig Extracts From Kunzea Ericoides; Phytoetherapy Research 19, 963-970 (2005).*
"Monarda Didyma Leaf Extract," *International Cosmetics Ingredient Dictionary and Handbook, 12 th* edition, Gottschalck and Bailey, Ed., *The Cosmetic, Toiletry and Fragrance Association*, Washington, D.C., 2:1605, 2008.
"Simmondsia Chinensis (Jojoba) Leaf Extract," *International Cosmetics Ingredient Dictionary and Handbook, 12th edition*, Gottschalck and Bailey, Ed., *The Cosmetic, Toiletry and Fragrance Association*, Washington, D.C., 2:2478-2479, 2008.

(Continued)

*Primary Examiner* — Patricia A Leith

(74) *Attorney, Agent, or Firm* — Norton Rose Fulbright US LLP

(57) ABSTRACT

Disclosed is a topical skin cleanser comprising *Silybum marianum* fruit extract, *Momordica grosvenorii* fruit extract, and a cosmetic vehicle comprising at least 50% by weight of the composition of water and disodium EDTA, glycerin, phenoxyethanol, triethanolamine, 3-Iodo-2-propynyl butyl carbamate, and benzyl alcohol.

4 Claims, No Drawings

(56) References Cited

U.S. PATENT DOCUMENTS

| | | | |
|---|---|---|---|
| 7,563,779 B2 | 7/2009 | Henderson et al. | 514/46 |
| 7,575,764 B2 | 8/2009 | Chen et al. | 424/725 |
| 7,575,772 B2 | 8/2009 | Shi et al. | 426/548 |
| 7,682,617 B2 | 3/2010 | Olalde | 424/195.15 |
| 7,687,065 B1 * | 3/2010 | Maor et al. | 424/401 |
| 7,700,084 B2 | 4/2010 | Delage-Grouiller | 424/78.03 |
| 7,722,904 B2 | 5/2010 | Schneider et al. | 424/746 |
| 7,749,535 B2 | 7/2010 | Mower et al. | 424/465 |
| 7,763,303 B2 | 7/2010 | Kenaschuk | 426/629 |
| 7,790,699 B2 | 9/2010 | Melvik et al. | 514/54 |
| 7,807,194 B2 | 10/2010 | Modliszewski | 424/451 |
| 7,816,341 B2 | 10/2010 | Sewall | 514/54 |
| 7,919,114 B2 | 4/2011 | Mower et al. | 424/465 |
| 8,022,038 B2 | 9/2011 | Miyata et al. | 514/17.2 |
| 8,034,755 B2 | 10/2011 | Kawano | 510/130 |
| 8,043,647 B1 | 10/2011 | Perry | 426/548 |
| 8,092,839 B2 | 1/2012 | Peskin | 424/725 |
| 2001/0014351 A1 | 8/2001 | Wang | 424/452 |
| 2005/0074421 A1 | 4/2005 | Tanaka | 424/401 |
| 2005/0271614 A1 * | 12/2005 | Wolfinbarger, Jr. | 424/70.14 |
| 2006/0003053 A1 | 1/2006 | Ekanayake et al. | 426/51 |
| 2006/0008426 A1 | 1/2006 | Doring et al. | 424/59 |
| 2006/0134095 A1 | 6/2006 | Ito et al. | 424/125 |
| 2006/0165641 A1 | 7/2006 | Pillai et al. | 424/70.22 |
| 2006/0233738 A1 * | 10/2006 | Miyata et al. | 424/74 |
| 2007/0116819 A1 | 5/2007 | Prakash et al. | 426/548 |
| 2007/0116832 A1 | 5/2007 | Prakash et al. | 426/548 |
| 2007/0116835 A1 | 5/2007 | Prakash et al. | 426/548 |
| 2007/0116838 A1 | 5/2007 | Prakash et al. | 426/548 |
| 2007/0116839 A1 | 5/2007 | Prakash et al. | 426/548 |
| 2007/0116841 A1 | 5/2007 | Prakash et al. | 426/548 |
| 2008/0033037 A1 | 2/2008 | Bernard et al. | 514/452 |
| 2008/0085295 A1 | 4/2008 | Melvik et al. | 424/423 |
| 2008/0107776 A1 | 5/2008 | Prakash et al. | 426/66 |
| 2008/0107787 A1 | 5/2008 | Prakash et al. | 426/548 |
| 2008/0108710 A1 | 5/2008 | Prakash et al. | 514/783 |
| 2008/0146472 A1 | 6/2008 | Brooks | 508/216 |
| 2008/0152698 A1 | 6/2008 | Effing | 424/445 |
| 2008/0279902 A1 | 11/2008 | Luria et al. | 424/401 |
| 2009/0041866 A1 | 2/2009 | Miyata et al. | 424/725 |
| 2009/0053378 A1 | 2/2009 | Prakash et al. | 426/548 |
| 2009/0137438 A1 | 5/2009 | Lepilleur | 514/54 |
| 2009/0186110 A1 | 7/2009 | Eidenberger | 424/774 |
| 2009/0246163 A1 | 10/2009 | Wahi | 424/78.03 |
| 2009/0263435 A1 * | 10/2009 | Potin et al. | 424/401 |
| 2009/0285917 A1 | 11/2009 | Jeong et al. | 424/740 |
| 2009/0311367 A1 | 12/2009 | Perry | 426/2 |
| 2009/0311404 A1 | 12/2009 | West et al. | 426/548 |
| 2009/0325885 A1 | 12/2009 | Miyata et al. | 514/21.5 |
| 2010/0021571 A1 | 1/2010 | Waugh et al. | 424/747 |
| 2010/0022462 A1 | 1/2010 | Shi | 514/25 |
| 2010/0143398 A1 | 6/2010 | Olalde | 424/195.15 |
| 2010/0196293 A1 | 8/2010 | Dal Farra | 424/725 |
| 2010/0227034 A1 | 9/2010 | Purkayastha et al. | 426/302 |
| 2010/0247453 A1 | 9/2010 | Jones | 424/48 |
| 2010/0255171 A1 | 10/2010 | Purkayastha et al. | 426/548 |
| 2010/0267847 A1 | 10/2010 | Yoshinaka et al. | 514/777 |
| 2010/0272838 A1 | 10/2010 | Prendergast | 424/758 |
| 2010/0278993 A1 | 11/2010 | Prakash et al. | 426/548 |
| 2010/0279946 A1 | 11/2010 | Dal Farra | 514/18.8 |
| 2010/0298251 A1 | 11/2010 | Kim et al. | 514/33 |
| 2010/0303914 A1 | 12/2010 | Melvik et al. | 536/30 |
| 2010/0310687 A1 | 12/2010 | Kim et al. | 424/758 |
| 2010/0310751 A1 | 12/2010 | Gelin et al. | 426/590 |
| 2011/0021456 A1 | 1/2011 | Lyndon et al. | 514/54 |
| 2011/0021614 A1 | 1/2011 | Cheng et al. | 514/452 |
| 2011/0044920 A1 | 2/2011 | Hines | 424/60 |
| 2011/0052737 A1 * | 3/2011 | Florence et al. | 424/742 |
| 2011/0129453 A1 * | 6/2011 | Harripersad | 424/94.1 |
| 2011/0151030 A1 | 6/2011 | Myhill et al. | 424/725 |
| 2011/0200712 A1 | 8/2011 | Takaichi | 426/74 |
| 2011/0201680 A1 | 8/2011 | Xu et al. | 514/456 |
| 2011/0212040 A1 | 9/2011 | Bezalel | 424/60 |
| 2011/0250250 A1 | 10/2011 | Kishida | 424/401 |
| 2011/0257110 A1 | 10/2011 | Kharazmi | 514/25 |
| 2011/0288165 A1 | 11/2011 | Bruheim | 514/458 |
| 2011/0300081 A1 | 12/2011 | Seneci | 424/43 |

FOREIGN PATENT DOCUMENTS

| | | | |
|---|---|---|---|
| JP | 10130137 | | 5/1998 |
| JP | 2001-316239 | | 11/2001 |
| JP | 2006-055038 | | 3/2006 |
| KR | 20020004706 A | * | 1/2002 |
| KR | 100773856 | | 11/2007 |
| WO | WO 2006/063402 | | 6/2006 |
| WO | WO 2006075236 | | 7/2006 |
| WO | WO 2006/087569 | | 8/2006 |
| WO | WO 2007/105864 | | 9/2007 |
| WO | WO 2010-039291 | | 6/2009 |
| WO | WO 2009-109946 | | 9/2009 |
| WO | WO 2010/066047 | | 6/2010 |
| WO | WO 2011/067313 | | 6/2011 |
| WO | WO 2011/116963 | | 9/2011 |
| WO | WO 2011/128783 | | 10/2011 |
| WO | WO 2011/147012 | | 12/2011 |
| WO | WO 2011/154958 | | 12/2011 |
| WO | WO 2012/003804 | | 1/2012 |

OTHER PUBLICATIONS

International Search Report arid Written Opinion issued in PCT Application No. PCT/US2011/068190, dated Aug. 30, 2012.
"Guava Extract." Natural Botanical Extracts, Carruba, Inc. Accessed online Dec. 16, 2010.
"Psidium Guajava Leaf Extract,"*International Cosmetics Ingredient Dictionary and Handbook, 12th edition*, Gottschalck and Bailey, Ed., *The Cosmetic, Toiletry and Fragrance Association*, Washington, D.C., 2:2309-2310, 2008.
Gutierrez et al., "*Psidium guajava*: a review of its traditional uses, phytochemistry and pharmacology," *Journal of Ethnopharmacology*, 117:1-27, 2008.
International Search Report and Written Opinion issued in PCT Application No. PCT/US2011/067635. dated Aug. 24, 2012.
Chabner et al. Perspectives: Chemotherapy and the War on Cancer; Nature Reviews. Cancer 5.1 (Jan. 2005): 65-72.
Tassone et al. Novel Therapeutic Approaches on the Targeting of Microenvironment-Derived Survival Pathways in Human Cancer: Experimental Models and Translational Issues; Current Pharmaceutical Design 13.5 (Feb. 2007): 487-96.
Office Action issued in Chinese Patent Application No. 201180066354, dated Jul. 17, 2014.
Wang, Jianxin Manual of Plant Materials Used in Cosmetics, Chemical Industry Press, p. 110-111, Jun. 2006.
Newton, David, et al. Medicinal Chemistry. Shanghai Scientific and Technical Literature Publishing House, p. 26-27, Jul. 2008: 26-27.

* cited by examiner

COSMETIC FORMULATION

CROSS REFERENCE TO RELATED APPLICATIONS

This application is a continuation of U.S. application Ser. No. 13/762,929, filed Feb. 8, 2013, which claims the benefit of U.S. Provisional Application Nos. 61/596,990, filed Feb. 9, 2012, and 61/597,011, filed Feb. 9, 2012. The contents of the referenced applications are incorporated into the present application by reference.

BACKGROUND OF THE INVENTION

A. Field of the Invention

The present invention relates generally to cosmetic compositions that can be used on dry skin, oily skin, normal skin, or combination skin. In particular embodiments, the compositions are cosmetic cleansers that can be used to cleanse or wash skin.

B. Description of Related Art

There are thousands of skin formulations available to consumers. Further, there are a myriad of different skin types among the population. Such skin types range from normal skin, dry skin, oily skin, and combination skin (e.g., normal/dry, normal/oily, dry/oily). This leads to a confusing and exhaustive search for different products for different applications.

Cosmetic cleansers are known and used in the marketplace. For instance, several cleansers include high levels of surfactants and alcohol, which can be caustic or irritating to skin. Further, while some water-based cleansers exist, the use of high amounts of water generally precludes the addition of other ingredients that can be beneficial to skin (e.g., moisturizers and skin actives). Also, by using high amounts of water, one is typically precluded from using a standard base that can be used for various skin-types.

SUMMARY OF THE INVENTION

Applicant has discovered a solution to the problems associated with current cosmetic cleansers. This solution is a combination of botanical ingredients that can be used to create a cleansing formulation for a particular skin-type (e.g., dry skin, normal skin, oil-skin, combination skin—e.g., normal/dry, normal/oily, dry/oily), while using a base-set of ingredients in the underlying cosmetic vehicle. Further, the amounts of the base-set of ingredients used in the underlying cosmetic vehicle can be modified to account for the particular combinations of botanical ingredients.

In one aspect, there is disclosed topical skin cleanser comprising *Silybum marianum* fruit extract, *Momordica grosvenorii* fruit extract, and a cosmetic vehicle comprising at least 50% by weight of the composition of water and disodium EDTA, glycerin, phenoxyethanol, triethanolamine, 3-Iodo-2-propynyl butyl carbamate, and benzyl alcohol. The cleanser can include 0.01 to 0.2% by weight of disodium EDTA, 2 to 7%% by weight of glycerin, 0.01 to 1% by weight of phenoxyethanol, 0.01 to 1% by weight of triethanolamine, 0.01 to 1% by weight of 3-Iodo-2-propynyl butyl carbamate, and 0.1 to 1% by weight of benzyl alcohol. The cleanser can include 0.001 to 0.1% by weight of *Silybum marianum* fruit extract and 0.001 to 0.1% by weight of *Momordica grosvenorii* fruit extract. The cleanser can be formulated for dry skin and further include hydrolyzed algin, and *Linum usitatissimum* seed extract. In one aspect, the cleanser can include 0.001 to 0.1% by weight of hydrolyzed algin and 0.001 to 0.1% to 0.0006% by weight of *Linum usitatissimum* seed extract. The cleanser formulated for dry skin can further include 70 to 80% by weight of water and glyceryl stearate, PEG-6 caprylic/capric glycerides, cetyl alcohol, stearyl alcohol, petrolatum, and *butyrospermum parkii*. In another aspect, the cleanser can be formulated for normal skin and further include *Plumeria alba* flower extract, and *Nymphaea gigantea* flower extract. The cleanser can include 0.001 to 0.1% by weight of *Plumeria alba* flower extract and 0.001 to 0.1% by weight of *Nymphaea gigantea* flower extract. The cleanser formulated for normal skin can further include 65 to 75% by weight of water and PEG-8, sunflower oil, cetearyl octanoate, dicapryl carbonate, glyceryl isostearate, stearic acid, and glyceryl stearate/PEG-100 stearate. In a further aspect, the cleanser can be formulated for oily skin and further include *Kunzea ericoides* leaf extract and *Psidium guajava* fruit extract. The cleanser can include 0.001 to 0.1% by weight of *Kunzea ericoides* leaf extract and 0.001 to 0.1% by weight of *Psidium guajava* fruit extract. The cleanser formulated for oily skin can include 50 to 60% by weight of water and propylene glycol, TEA-lauryl sulfate, cocamidopropyl betaine, sodium methyl cocoyltaurate, dimethicone, and lauramine oxide. Also disclosed is a method of applying the topical skin cleanser to skin comprising applying said cleanser to skin followed by rinsing said cleanser from the skin within 5 minutes after topical application. This can remove dirt, sebum, and/or make-up from the skin. In some instances, a toner can be applied to the skin within 5 minutes after the skin has been cleansed by said skin cleanser.

In another embodiment, there is disclosed a topical skin composition that includes a combination of botanical extracts, said extracts including *Silybum marianum* fruit extract and *Momordica grosvenorii* fruit extract and a cosmetic vehicle that includes at least 70% by weight of water (based on total weight of the composition), and in particular aspects, 70 to 80% by weight of water. This combination can be used across all skin types (e.g., dry skin, normal skin, oily skin, and combination skin) The addition of hydrolyzed algin and *Linum usitatissimum* seed extract to this combination was found to work particularly well with dry skin, as it can restore the natural pH balance in skin while leaving the skin feeling smooth, hydrated, and refreshed. The addition of *Plumeria alba* flower extract, and *Nymphaea gigantea* flower extract was found to work particularly well with normal skin, as it can leave the skin feeling both clean and soft. Further, this combination can remove excess oil. The addition of *Kunzea ericoides* leaf extract and *Psidium guajava* fruit extract was found to work particularly well with oily skin, as it can purify the skin, cleanse clogged pores, and remove excess oil or sebum without drying the skin. The amounts of these botanical plant extracts within a given composition can vary. In one instance, for example, the following ranges/amounts were found to work well: 0.001 to 0.002% by weight of *Silybum marianum* fruit extract; and 0.0004 to 0.0006% by weight of *Momordica grosvenorii* fruit extract. For dry skin, the addition of the following botanical plant extracts in the following amounts were found to work well: 0.002 to 0.004% by weight of hydrolyzed algin; and 0.0004 to 0.0006% by weight of *Linum usitatissimum* seed extract. For normal skin, the addition of the following botanical plant extracts in the following amounts were found to work well: 0.01 to 0.02% by weight of *Plumeria alba* flower extract; and 0.001 to 0.01% by weight of *Nymphaea gigantea* flower extract. For oily skin, the addition of the following botanical plant extracts in the following amounts were found to work well: 0.005 to 0.01% by weight of *Kunzea ericoides* leaf extract; and 0.0004 to 0.0006% by weight of *Psidium guajava* fruit extract. It is also contemplated, however, that the amount of said botanical plant extracts can go below or above the stated ranges. In this regard, the amount of any one of said botanical plant extracts within a given composition can range from 0.00001 to 10%, 0.0001 to 5%, 0.001 to 2%, 0.01 to 1%, 0.1 to 0.5%, etc.

In particular aspects, and in addition to the high amounts of water, the cosmetic vehicle can also include any one of, any combination of, or at least 1, 2, 3, 4, 5, 6, 7, 8, 9, or all 10 of the following ingredients: glycerin; triethanolamine; DMDM hydantoin; disodium EDTA; butylene glycol; methylparaben; phenoxyethanol; potassium sorbate; citric acid; and sodium benzoate. In particular aspects, it was found that a combination of all 11 of these additional ingredients can be used as vehicle for products designed for dry skin, normal skin, oily skin, and combination skin. This is a unique discovery, as underlying vehicles for particular skin types tend to be different to serve different needs (e.g., dry skin typically needs excess moisturizing abilities, whereas oily skin typically needs reduced moisturizing abilities, etc.). The general range/amounts for each of these ingredients in the vehicle can be (based on total weight of the composition): 2 to 6% by weight of glycerin; 0.1 to 1% by weight of triethanolamine; 0.004 to 0.2% by weight of DMDM hydantoin; 0.01 to 0.2% by weight of disodium EDTA; 0.01 to 0.2% by weight of butylene glycol; 0.001 to 0.2% by weight of methylparaben; 0.0001 to 0.002% by weight of phenoxyethanol; 0.0001 to 0.0005% by weight of potassium sorbate; 0.0001 to 0.0003% by weight of citric acid; and 0.0002 to 0.0004% by weight of sodium benzoate. The amounts of ingredients within the cosmetic vehicle or the addition of excipients or other ingredients can also be added to the cosmetic vehicle to, for example, modify the vehicle's rheological properties, change the combination of botanical plant extracts, or include additional skin benefits. In one particular instance, the following vehicle was found to work well with dry skin (amounts based on total weight of the composition): 70 to 80% by weight of water; 2 to 4% by weight of glycerin; 0.4 to 0.6% by weight of triethanolamine; 0.1 to 0.2% by weight of DMDM hydantoin; 0.01 to 0.2% by weight of disodium EDTA; 0.03 to 0.1% by weight of butylene glycol; 0.005 to 0.007% by weight of methylparaben; 0.001 to 0.002% by weight of phenoxyethanol; 0.0003 to 0.0005% by weight of potassium sorbate; 0.0002 to 0.0003% by weight of citric acid; and 0.0002 to 0.0003% by weight of sodium benzoate. In another instance, the following vehicle was found to work well with normal skin (amounts based on total weight of the composition): 70 to 80% by weight of water; 5 to 6% by weight of glycerin; 0.4 to 0.6% by weight of triethanolamine; 0.1 to 0.2% by weight of DMDM hydantoin; 0.1 to 0.2% by weight of disodium EDTA; 0.1 to 0.2% by weight of butylene glycol; 0.005 to 0.01% by weight of methylparaben; 0.0004 to 0.0005% by weight of phenoxyethanol; 0.0002 to 0.0003% by weight of potassium sorbate; 0.0001 to 0.0002% by weight of citric acid; and 0.0002 to 0.0003% by weight of sodium benzoate. In still another instance, the following vehicle was found to work well with oily skin (amounts based on total weight of the composition): 70 to 80% by weight of water; 2 to 4% by weight of glycerin; 0.7 to 0.9% by weight of triethanolamine; 0.004 to 0.006% by weight of DMDM hydantoin; 0.1 to 0.2% by weight of disodium EDTA; 0.07 to 0.2% by weight of butylene glycol; 0.1 to 0.2% by weight of methylparaben; 0.0001 to 0.0002% by weight of phenoxyethanol; 0.0003 to 0.0004% by weight of potassium sorbate; 0.0002 to 0.0003% by weight of citric acid; and 0.0003 to 0.0004% by weight of sodium benzoate. Also, and as previously indicated, the compositions of the present invention work well as cleansers. One of the reasons for this is their light weight and mild/gentle skin formulation characteristics.

Also disclosed is a method of applying any one of the topical skin compositions of the present invention to skin. The skin can be facial skin, body skin (e.g., arms, hands, legs, feet, neck, back chest, abdomen, or scalp. The composition can be applied and rubbed into skin and then rinsed from the skin (for example, with water) within 1, 2, 3, 4, 5, 6, 7, 8, 9, or 10 minutes after topical application. The compositions can be used to cleanse skin by removing unwanted dirt, oil, sebum, make-up or other foreign materials on the skin. Further, a skin toner or moisturizer product can be applied to skin within 1, 2, 3, 4, 5, 6, 7, 8, 9, or 10 minutes after rinsing any one of the topical skin compositions to skin. In this sense, the topical skin compositions of the present invention can be used in a regimen of other products. For instance, a person could start with cleansing the skin with the compositions of the present invention, followed by topical application of a toner, and/or a moisturizer product to skin, and in some instances, followed by cleansing the skin for application of a mask (typically during the evening hours).

In a further embodiment, the inventors contemplate the use of the compositions of the present invention to treat particular skin conditions. The skin conditions can range from fine lines or wrinkles, uneven skin tone, loose or saggy skin, erythemic skin, sensitive skin, dry skin, flaky skin, itchy skin, chapped skin, pruritus, spider veins, lentigo, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, and/or skin-inflammatory skin conditions.

The compositions of the present invention can take the form of a spray, foam, cream ointment, gel, or lotion, emulsion, solution, be aerosolized, or be in powdered form. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

The compositions and methods for their use can "comprise," "consist essentially of," or "consist of" any of the ingredients disclosed throughout the specification. For purposes of consisting essentially of means that inclusion of additional ingredients in the compositions do not materially affect the properties of the aforementioned combination of botanical plant extracts and cosmetic vehicle. One such instance would be the inclusion of an ingredient that has a detrimental effect (e.g., reducing the efficacy or stability) on any one of the ingredients identified said combination or on the overall effect of the composition (e.g., ability to cleanse skin).

"Acne" includes pimples, black heads, white heads, papules, nodules, pustules, inflammatory lesions, or cysts.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "treating" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Given the number of various products on the market today and the myriad of different skin-types, a person is oftentimes at a loss to identify an appropriate product for an appropriate skin type.

The cosmetic cleansers of the present invention can be used to clean, maintain and improve the health of a variety of skin types. For instance, the cleansers can provide many advantages including: removal of impure elements such as sebum from the skin; remove make-up and other foreign objects from the skin, unclog skin pores; correct or balance the pH levels of upset skin; refresh and rejuvenate the skin; smoothen and tighten skin pores; and prepare the skin for subsequent application of a skin toner or moisturizer product. In this sense, the compositions of the present invention utilize unique combinations of botanical ingredients, which can be used to create a formulation for a particular skin type (e.g., normal, dry, oily, or combination skin), and an underlying base set of ingredients for the cosmetic vehicle.

These and other non-limiting aspects of the present invention are described in further detail below.

A. Cleansers

People who use cosmetic products oftentimes use a variety of different products throughout the day. Such a regimen can include cleansing the skin followed by toning the skin, followed by moisturizing the skin. In some instances, people will also use cosmetic masks in the evening, which can be a heavier product that provides deep and prolonged cleansing, exfoliating, and/or moisturization of the skin.

As the name suggests, cleansers are designed to cleanse the skin by removing dirt, cosmetic products, sebum, and other unwanted material from the skin. Problems with existing cleansers are several fold ranging from having high amounts of skin irritating substances, leaving residual elements on the skin (e.g., soapy film), and changing the pH levels of the surface of the skin, which can result in irritated or reddened skin.

The cleansers of the present invention, however, can be used across all skin types while reducing any skin irritating effects. For instance, while the cleansers of the present invention can cleanse skin, they can also maintain the skin's natural pH balance by not stripping essential elements from the skin. The cleansers can also leave the skin feeling smooth, hydrated, and refreshed. As such, the cleansers of the present invention have a multitude of beneficial properties other than just cleansing skin. These beneficial properties are derived from the unique combination of botanical ingredients, which can be used for a given skin type along with an underlying cosmetic vehicle, which can be used across all skin types. Therefore, the combination of the botanical ingredients with the cosmetic vehicle provides a unique cleansing formulation with wide ranging applications.

B. Determining Skin-Type

A first step in using the cleansers of the present invention can be to determine a user's skin type. As noted above, there are three main skin types: (1) normal skin; (2) dry skin; and (3) oily skin. A fourth skin type is simply a combination of any one of normal, dry, or oily skin (e.g., normal/dry, normal/oily, oily/dry). There are also well-known methods for determining a person's skin type.

For instance, normal skin can be identified as having a smooth texture and no greasy patches or flaky areas. Therefore, a product that can retain skin moisture in its present form can be used to maintain the appearance of normal skin.

As for dry skin, it has a low level of sebum production from sebaceous glands and is prone to irritation or erythema. The appearance of dry skin has a parched look caused by the skin's inability to retain moisture. Oftentimes it feels "tight" and uncomfortable after washing and is prone to chapping, flaking, and cracking Dry skin can be exacerbated by wind, extremes of temperature and air-conditioning, all of which cause the skin to flake, chap and feel tight. Dry skin typically has a dull appearance. Therefore, a product that deliver appropriate hydration and restore moisture to dry skin can be used to counteract the effects of dry skin.

With respect to oily skin, such skin is shiny, thick and dull colored. It feels oily and has coarse pores and pimples and other unsightly blemishes due to overproduction of sebum from sebaceous glands and from clogged/blocked pores. In this regard, oily skin usually has oil producing sebaceous glands that are overactive and produce more oil than is needed. The oil oozes and gives the skin a greasy shine. The pores are enlarged and the skin has a coarse look. Therefore, a product that can help control skin surface oiliness while also cleansing clogged pores can be used to counteract the effects of oily skin.

As noted above, combination skin is a combination of both oily, dry, and/or normal skin (e.g., normal/dry, oily/dry, normal/oily). For oily/dry skin, there is typically a greasy center panel consisting of nose, forehead and chin (also known as the "T-zone" of a person's face) and a dry panel consisting of cheeks, mouth and the areas around the eyes. Therefore, a product that can control the excess oil production in sebaceous glands in the T-zone while also hydrating the dry skin areas outside of the T-zone can be used for such oily/dry skin.

Once a particular skin-type is identified, a person can then select an appropriate composition to correct or maintain the skin-type.

C. Botanical Combinations

The inventors discovered that the combination of a particular set of botanical extracts with an underlying cosmetic vehicle works well across all skin types. Such a product can be particularly beneficial for combination skin or for skin that may be in between dry skin and normal skin, normal skin and oily skin, or dry skin and oily skin. The combination of botanicals that can be used across all skin types includes *Silybum marianum* fruit extract and *Momordica grosvenorii* fruit extract.

Milk thistle (*Silybum marianum*) is a plant native to Southern Europe and Asia. It is known for producing red to purple flowers, shiny pale green leaves with white veins, and fruit. The *Silybum marianum* extract of the present invention can be a hydroalcoholic (water and alcohol denat) extract that includes silymarin as an active ingredient (silymarin is a mixture of flavanonol derivatives that includes silibine, silicristine, silidianin, isosolibine, and isosilicristine). The fruit portion of *Silybum marianum* includes silymarin. The *Silybum marianum* extract can be obtained from the fruit portion of this plant by mascerating the fruit pulp and then subjecting the pulp to a hydroalcoholic solution of water and SD alcohol 39-C (alcohol denat.) to obtain the extract. The extract can then filtered and packaged for storage or be added to a composition of the present invention. In addition to this extraction process, *Silybum marianum* extract can be purchased from Provital S.A (SPAIN) under the trade names PRONALEN SILYMARIN HSC or PRONALEN SILYMARIN SPE.

Luo han guo (*Momordica grosvenori*) is a perennial vine that grows 3-5 meters long with narrow heart shaped leaves and green round fruit 5-7 cm in diameter. This plant is native to southern China. The fruit has been used as a natural food sweetener in China for several decades. The luo han guo extract of the present invention can be obtained from the fruit portion of this plant by macerating the fruit pulp and then subjecting the pulp to a hydroglycolic solution of water, glycerin, and preservatives to obtain the extract. The extract can then filtered and packaged for storage or be added to a composition of the present invention. In addition to this extraction process, luo han guo fruit extract can be purchased from Carrubba Inc., Milford, Conn. (USA).

1. Dry Skin

The addition of *Linum usitatissimum* seed extract and hydrolyzed algin to the *Silybum marianum* fruit extract and the *Momordica grosvenori* fruit combination was found to work well on dry skin.

Flax seed (*Linum usitatissimum* (Linseed)) is an annual, biennial or perennial herb that can reach 3 feet in height. It includes a slender stem, lance-shaped leaves, and can produce ski-blue flowers and oily brown seeds. This plant is native to Europe and Asia. The flax seed extract of the present invention can be obtained from the seed portion of this plant by macerating the seed and then subjecting the seed to a hydroglycolic solution of water and glycerin to obtain the extract. The extract can then filtered and packaged for storage or be added to a composition of the present invention. In addition to this extraction process, flax seed extract can be purchased from Carrubba Inc., Milford, Conn. (USA).

Hydrolyzed algin can be obtained from *Laminaria digitata*, which is a brown alga, that is found in the littoral zone of bodies of water. The hydrolyzed algin can be an aqueous solution of an oligosaccharide that can be produced by controlled enzymatic depolymerization of membranous polysaccharides from *Laminaria digitata*. The structure of the oligosaccharide is a chain of 2 uronic acids: mannuronic and guluronic, which can be illustrated as follows:

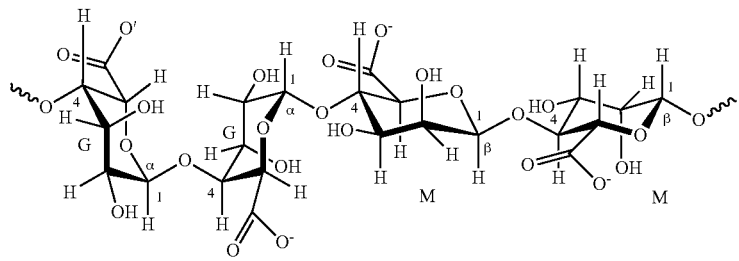

In addition to this production process, hydrolyzed algin can be purchased from Barnet Products Corp., Englewood Cliffs, N.J. (USA) under the trade name PHYKO AL-PF.

2. Normal Skin

The addition of *Plumeria alba* flower extract and *Nymphaea gigantea* flower extract to the *Silybum marianum* fruit extract and *Momordica grosvenorii* fruit extract combination was found to work well on normal skin.

*Plumeria alba* (Frangipani) is a large evergreen shrub with narrow elongated leaves and large white followers that have a yellow center . It is native to Central America and the Caribbean. The frangipani flower extract of the present invention can be obtained from the flower portion of this plant by macerating the flower and then subjecting the flower to an aqueous extraction process. The extract can then be filtered, placed in a butylene glycol solution, and packaged for storage or be added to a composition of the present invention. In addition to this extraction process, frangipani flower extract can be purchased from Southern Cross Botanicals, New South Wales (AUSTRALIA) under the trade name ABACROSS FRANGIPANI FLOWER BG.

*Nymphea gigantea* (Giant Water Lily) is a tropical plant that is native to the tropical and subtropical regions of Australia. This plant can produce large (up to 25 cm) blue-white flowers that emerge from the water and large circular leaves that grow up to 75 cm in diameter. The *Nymphea gigantea* flower extract of the present invention can be obtained from the flower portion of this plant by macerating the flower and then subjecting the flower to an aqueous extraction process. The extract can then be filtered, placed in a butylene glycol solution, and packaged for storage or be added to a composition of the present invention. In addition to this extraction process, frangipani flower extract can be purchased from Southern Cross Botanicals, New South Wales (AUSTRALIA) under the trade name ABACROSS WATER LILY BG.

3. Oily Skin

The addition of *Psidium guajava* fruit extract and *Kunzea ericoides* leaf extract to the *Silybum marianum* fruit extract and *Momordica grosvenorii* fruit extract combination was found to work well on oily skin.

Guava or *Psidium guajava* is an evergreen tree or shrub that can reach 6 to 25 feet in height. It produces green leaves, fragrant white flowers, and fruit. The fruit is pear-shaped and 3 to 6 cm in length. When ripe, the skin of the fruit has a reddish-yellow color. This plant is native to the region spanning Mexico to northern South America. The fruit portion of guava is used in the context of the present invention to obtain the extract. The guava fruit extract of the present invention can be produced by macerating the fruit pulp and then subjecting the pulp to a hydroglycolic solution of water and glycerin to obtain the extract. The extract can then be filtered and packaged for storage. In addition to this extraction process, guava fruit extract of the present invention can be purchased from Carrubba Inc., Milford, Conn. (USA).

Kanuka or *Kunzea ericoides* is a tree that can reach up to 30 meters in height. The leaves have an oval shape and the flowers are white. This plant is native to Australia and New Zealand. The *Kunzea ericoides* leaf extract of the present invention can be obtained from the leaf portion of this plant by macerating the leaf and then subjecting the leaf to an aqueous extraction process. The extract can then be filtered, placed in a butylene glycol solution, and packaged for storage or be added to a composition of the present invention. In addition to this extraction process, kanuka leaf extract can be purchased from Southern Cross Botanicals, New South Wales (AUSTRALIA) under the trade name ABACROSS KANUKA BG.

D. Cosmetic Vehicle

As noted above, the inventors discovered two separate cosmetic vehicles that can be used to create a cleanser for various skin types. That is, these vehicles can be used in cleansers designed for dry skin, oily skin, normal skin, and combination skin. In one instance, the vehicle can include at least 50% by weight of the composition of water and disodium EDTA, glycerin, phenoxyethanol, triethanolamine, 3-Iodo-2-propynyl butyl carbamate, and benzyl alcohol. The cleanser can include 0.01 to 0.2% by weight of disodium EDTA, 2 to 7%% by weight of glycerin, 0.01 to 1% by weight of phenoxyethanol, 0.01 to 1% by weight of triethanolamine, 0.01 to 1% by weight of 3-Iodo-2-propynyl butyl carbamate, and 0.1 to 1% by weight of benzyl alcohol. In another instance, the vehicle can include at least 70% w/w of the cleanser composition of water, and in particular aspects, 70 to 80% w/w of water. In addition, it also includes glycerin, triethanolamine, DMDM hydantoin, disodium EDTA, butylene glycol, methylparaben, phenoxyethanol, potassium sorbate, citric acid, and sodium benzoate. As discussed in the summary of the invention section, the amounts of the ingredients within the cosmetic vehicle can vary to establish a desired consistency or rheological property and to account for additional botanical ingredients being added. Further the vehicle can even include further ingredients as desired. Suppliers for each of these ingredients are readily available (see, e.g., (CTFA, 12$^{th}$ Edition, Volumes 1-4 (2008), the relevant sections of which are incorporated by reference).

E. Amounts/Concentration Ranges

In addition to what has previously been discussed, it is also contemplated that the compositions of the present invention can include any amount of the ingredients or additional cosmetic or pharmaceutical ingredients described in this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

F. Additional Ingredients

In addition to the botanical extracts and cosmetic vehicle ingredients, the compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. *aloe vera*, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., *aloe* extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *aloe barbadensis, aloe-barbadensis* extract, *aloe barbadensis* gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, maltitol, matricaria (*chamomilla recutita*) oil, methyl glucose sesquistearate, methylsilanol PCA, mineral oil, mink oil, *mortierella oil*, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof e. Emulsifiers In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof 2. Pharmaceutical Ingredients Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

G. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

The formulations in Tables 1-8 are each cleansers. The Tables 1 and 5 formulations are generic formulations. The generic formulations can be used for all skin types (dry, normal, oily, combination). The Tables 2 and 6 formulations are designed for dry skin. The Tables 3 and 7 formulations are designed for normal skin. The Tables 4 and 8 formulations are designed for oily skin.

TABLE 1*

| Ingredient | % Concentration (by weight) |
| --- | --- |
| Water | q.s. |
| Disodium EDTA | 0.001 to 0.2 |
| Glycerin | 2 to 7 |
| Phenoxyethanol | 0.01 to 1 |
| Triethanolamine | 0.01 to 1 |
| Glycacil 2000** | 0.01 to 1 |
| Benzyl Alcohol | 0.1 to 1 |
| Silybum marianum fruit extract*** | 0.001 to 0.1 |
| Momordica grosvenorii fruit extract**** | 0.001 to 0.1 |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological or tactile properties of the composition. If additional ingredients are added, then they can be q.s.'d in amounts so long as the amount of water in the composition is between 50 to 80% w/w (see Tables 2-4).
**Glycacil 2000 includes 3-Iodo-2-propynyl butyl carbamate. It can be purchased from Lonza, Inc. Allendale, New Jersey.
***Obtained from Provital S.A (SPAIN) under the trade name PRONALEN SILYMARIN HSC.
****Obtained from Carrubba Inc., Milford, Connecticut (USA).

TABLE 2*

| Ingredient | % Concentration (by weight) |
|---|---|
| Water | 74 |
| Disodium EDTA | 0.1 |
| Glycerin | 3 |
| Phenoxyethanol | 0.8 |
| Triethanolamine | 0.5 |
| Glycacil 2000** | 0.3 |
| Benzyl Alcohol | 0.9 |
| *Silybum marianum* fruit extract*** | 0.05 |
| *Momordica grosvenorii* fruit extract**** | 0.05 |
| Hydrolyzed algin***** | 0.05 |
| *Linum usitatissimum* seed extract****** | 0.05 |
| Excipients******* | q.s. |

*Formulation can be prepared by mixing the ingredients in a beaker under heat 70-75° C. until homogenous. Subsequently, the formulation can be cooled to standing room temperature (20-25° C.).
**Glycacil 2000 includes 3-Iodo-2-propynyl butyl carbamate. It can be purchased from Lonza, Inc. Allendale, New Jersey.
***Obtained from Provital S.A (SPAIN) under the trade name PRONALEN SILYMARIN HSC.
****Obtained from Carrubba Inc., Milford, Connecticut (USA).
*****Obtained from Barnet Products Corp., Englewood Cliffs, New Jersey (USA) under the trade name PHYKO AL-PF.
******Obtained from Carrubba Inc., Milford, Connecticut (USA).
*******The following excipients were found to work well for people with dry skin: glyceryl stearate; PEG-6 caprylic/capric glycerides; cetyl alcohol; stearyl alcohol; petrolatum; and *butyrospermum parkii*. The amounts of said excipients can be modified as desired to create a particular tactile property (e.g., equal amounts can be used or amounts of greater than 1% can be used).

TABLE 3*

| Ingredient | % Concentration (by weight) |
|---|---|
| Water | 71 |
| Disodium EDTA | 0.1 |
| Glycerin | 5.5 |
| Phenoxyethanol | 0.9 |
| Triethanolamine | 0.4 |
| Glycacil 2000** | 0.3 |
| Benzyl Alcohol | 0.6 |
| *Silybum marianum* fruit extract*** | 0.05 |
| *Momordica grosvenorii* fruit extract**** | 0.05 |
| *Plumeria alba* flower extract***** | 0.05 |
| *Nymphaea gigantea* flower extract****** | 0.05 |
| Excipients******* | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition. If additional ingredients are added, then they can be q.s.'d in amounts so long as the amount of water in the composition is at least 70% w/w, and preferably between 70 to 80% w/w.
**Glycacil 2000 includes 3-Iodo-2-propynyl butyl carbamate. It can be purchased from Lonza, Inc. Allendale, New Jersey.
***Obtained from Provital S.A (SPAIN) under the trade name PRONALEN SILYMARIN HSC.
****Obtained from Carrubba Inc., Milford, Connecticut (USA).
*****Obtained from Southern Cross Botanicals, New South Wales (AUSTRALIA) under the trade name ABACROSS FRANGIPANI FLOWER BG.
******Obtained from Southern Cross Botanicals, New South Wales (AUSTRALIA) under the trade name ABACROSS WATER LILY BG.
*******The following excipients were found to work well for people with normal skin: PEG-8; sunflower oil; cetearyl octanoate; dicapryl carbonate; glyceryl isostearate; stearic acid; and glyceryl stearate/PEG-100 stearate. The amounts of said excipients can be modified as desired to create a particular tactile property (e.g., equal amounts can be used or amounts of greater than 1% can be used).

TABLE 4*

| Ingredient | % Concentration (by weight) |
|---|---|
| Water | 56 |
| Disodium EDTA | 0.1 |
| Glycerin | 3 |
| Capryl Glycol/Phenoxyethanol | 1.3 |
| Triethanolamine | 0.9 |
| Glycacil 2000** | 0.2 |
| Benzyl Alcohol | 0.5 |
| *Silybum marianum* fruit extract*** | 0.05 |
| *Momordica grosvenorii* fruit extract**** | 0.05 |
| *Kunzea ericoides* leaf extract***** | 0.05 |
| *Psidium guajava* fruit extract****** | 0.05 |
| Excipients******* | q.s. |

*Formulation can be prepared by mixing the ingredients in a beaker under heat 70-75° C., until homogeneous. Subsequently, the formulation can be cooled to standing room temperature (20-25° C.).
**Glycacil 2000 includes 3-Iodo-2-propynyl butyl carbamate. It can be purchased from Lonza, Inc. Allendale, New Jersey.
***Obtained from Provital S.A (SPAIN) under the trade name PRONALEN SILYMARIN HSC.
****Obtained from Carrubba Inc., Milford, Connecticut (USA).
*****Obtained from Southern Cross Botanicals, New South Wales (AUSTRALIA) under the trade name ABACROSS KANUKA BG.
******Obtained from Carrubba Inc., Milford, Connecticut (USA).
*******The following excipients were found to work well for people with oily skin: propylene glycol; TEA- lauryl sulfate; cocamidopropyl betaine; sodium methyl cocoyltaurate; dimethicone; and lauramine oxide. The amounts of said excipients can be modified as desired to create a particular tactile property (e.g., equal amounts can be used or amounts of greater than 1% can be used).

TABLE 5*

| Ingredient | % Concentration (by weight) |
|---|---|
| Water | q.s. (at least 70% by weight of water) |
| Glycerin | 2 to 6 |
| Triethanolamine | 0.1 to 1 |
| DMDM Hydantoin | 0.004 to 0.2 |
| Disodium EDTA | 0.01 to 0.2 |
| Butylene Glycol | 0.01 to 0.2 |
| Methylparaben | 0.001 to 0.2 |
| Phenoxyethanol | 0.0001 to 0.002 |
| Potassium sorbate | 0.0001 to 0.0005 |
| Citric acid | 0.0001 to 0.0003 |
| Sodium benzoate | 0.0001 to 0.0003 |
| *Silybum marianum* fruit extract** | 0.001 to 0.002 |
| *Momordica grosvenorii* fruit extract*** | 0.0004 to 0.0006 |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition. If additional ingredients are added, then they can be q.s.'d in amounts so long as the amount of water in the composition is at least 70% w/w, and preferably between 70 to 80% w/w.
**Obtained from Provital S.A (SPAIN) under the trade name PRONALEN SILYMARIN HSC.
***Obtained from Carrubba Inc., Milford, Connecticut (USA).

TABLE 6*

| Ingredient | % Concentration (by weight) |
|---|---|
| Water | 76 |
| Glycerin | 3 |
| Triethanolamine | 0.5 |
| DMDM Hydantoin | 0.2 |
| Disodium EDTA | 0.1 |
| Butylene Glycol | 0.04 |
| Methylparaben | 0.007 |
| Phenoxyethanol | 0.002 |
| Potassium Sorbate | 0.0004 |
| Citric Acid | 0.0003 |
| Sodium Benzoate | 0.0003 |
| *Silybum marianum* fruit extract** | 0.002 |
| *Momordica grosvenorii* frit extract*** | 0.0005 |

TABLE 6*-continued

| Ingredient | % Concentration (by weight) |
| --- | --- |
| Hydrolyzed algin**** | 0.004 |
| *Linum usitatissimum* seed extract***** | 0.0005 |
| Excipients****** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition. If additional ingredients are added, then they can be q.s'd in amounts so long as the amount of water in the composition is at least 70% w/w, and preferably between 70 to 80% w/w.
**Obtained from Provital S.A (SPAIN) under the trade name PRONALEN SILYMARIN HSC.
***Obtained from Carrubba Inc., Milford, Connecticut (USA).
****Obtained from Barnet Products Corp., Englewood Cliffs, New Jersey (USA) under the trade name PHYKO AL-PF.
*****Obtained from Carrubba Inc., Milford, Connecticut (USA).
******Excipients such as thickeners, oils, and humectants were used to modify the viscosity of the composition and change its tactile properties. A person of ordinary skill in the art can make such modifications as desired.

TABLE 7*

| Ingredient | % Concentration (by weight) |
| --- | --- |
| Water | 73 |
| Glycerin | 5.5 |
| Triethanolamine | 0.5 |
| DMDM Hydantoin | 0.1 |
| Disodium EDTA | 0.1 |
| Butylene Glycol | 0.1 |
| Methylparaben | 0.006 |
| Phenoxyethanol | 0.005 |
| Potassium Sorbate | 0.0003 |
| Citric Acid | 0.0001 |
| Sodium Benzoate | 0.0003 |
| *Silybum marianum* fruit extract** | 0.002 |
| *Momordica grosvenorii* fruit extract*** | 0.0005 |
| *Plumeria alba* flower extract**** | 0.01 |
| *Nymphaea gigantea* flower extract***** | 0.01 |
| Excipients****** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition. If additional ingredients are added, then they can be q.s'd in amounts so long as the amount of water in the composition is at least 70% w/w, and preferably between 70 to 80% w/w.
**Obtained from Provital S.A (SPAIN) under the trade name PRONALEN SILYMARIN HSC.
***Obtained from Carrubba Inc., Milford, Connecticut (USA).
****Obtained from Southern Cross Botanicals, New South Wales (AUSTRALIA) under the trade name ABACROSS FRANGIPANI FLOWER BG.
*****Obtained from Southern Cross Botanicals, New South Wales (AUSTRALIA) under the trade name ABACROSS WATER LILY BG.
******Excipients such as thickeners, oils, and humectants were used to modify the viscosity of the composition and change its tactile properties. A person of ordinary skill in the art can make such modifications as desired.

TABLE 8*

| Ingredient | % Concentration (by weight) |
| --- | --- |
| Water | 76 |
| Glycerin | 3 |
| Triethanolamine | 0.8 |
| DMDM Hydantoin | 0.004 |
| Disodium EDTA | 0.1 |
| Butylene Glycol | 0.08 |
| Methylparaben | 0.1 |
| Phenoxyethanol | 0.0002 |
| Potassium Sorbate | 0.0004 |
| Citric Acid | 0.0003 |
| Sodium Benzoate | 0.0004 |
| *Silybum marianum* fruit extract** | 0.002 |
| *Momordica grosvenorii* fruit extract*** | 0.0005 |
| *Kunzea ericoides* leaf extract**** | 0.008 |
| *Psidium guajava* fruit extract***** | 0.0005 |
| Excipients****** | q.s. |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition. If additional ingredients are added, then they can be q.s'd in amounts so long as the amount of water in the composition is at least 70% w/w, and preferably between 70 to 80% w/w.
**Obtained from Provital S.A (SPAIN) under the trade name PRONALEN SILYMARIN HSC.
***Obtained from Carrubba Inc., Milford, Connecticut (USA).
****Obtained from Southern Cross Botanicals, New South Wales (AUSTRALIA) under the trade name ABACROSS KANUKA BG.
*****Obtained from Carrubba Inc., Milford, Connecticut (USA).
******Excipients such as thickeners, oils, and humectants were used to modify the viscosity of the composition and change its tactile properties. A person of ordinary skill in the art can make such modifications as desired.

Formulations having the characteristics of the Tables 2 and 5 formulations were used in a regimen that also included toner, moisturizer, and mask products. These formulations contributed to cleansing the skin and restoring the skin's natural pH balance, while also making the skin feeling smooth, hydrated, and nourished. Data was obtained from a one-week independent consumer study.

Formulations having the characteristics of the Tables 3 and 6 formulations were used in a regimen that also included toner, moisturizer, and mask products. These formulations contributed to cleansing the skin, while leaving the skin feeling soft. Data was obtained from a one-week independent consumer study.

Formulations having the characteristics of the Tables 4 and 8 formulations were used in a regimen that also included toner, moisturizer, and mask products. These formulations contributed in cleansing the skin and pores while leaving the skin feeling clean and reducing shine. Data was obtained from a one-week independent consumer study.

Example 2

(Additional Assays)

Additional assays that can be used to determine the efficacy of any one of the compositions disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. A composition of the present invention can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythemic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claim is:

1. A topical skin composition comprising:
   (a) *Silybum marianum* fruit extract;
   (b) *Momordica grosvenorii* fruit extract;
   (c) *Plumeria alba* flower extract;
   (d) *Nymphaea gigantea* flower extract; and
   (e) a cosmetic vehicle comprising:
      butylene glycol; and
      glycerin
   wherein the composition comprises at least 40% by weight of water.

2. The topical skin composition of claim 1, wherein the composition comprises 50 to 80 wt. % by weight of water.

3. The topical skin composition of claim 1 comprising:
   0.0001 to 0.1% by weight of *Silybum marianum* fruit extract; and
   0.0001 to 0.1% by weight of *Momordica grosvenorii* fruit extract.

4. A method of applying the topical skin composition of claim 1 to skin comprising applying said composition to skin.

* * * * *